US008028561B2

(12) United States Patent
Herz et al.

(10) Patent No.: US 8,028,561 B2
(45) Date of Patent: Oct. 4, 2011

(54) HYDROGEN SENSOR WITH AIR ACCESS

(75) Inventors: Joshua J. Herz, Rochester, NY (US); Wendy Dannels, Rochester, NY (US); Robert E. Taylor, Fairport, NY (US); Steven E. Mulvaney, Livonia, NY (US)

(73) Assignee: Qualitrol Company, LLC, Fairport, NY (US)

( * ) Notice: Subject to any disclaimer, the term of this patent is extended or adjusted under 35 U.S.C. 154(b) by 571 days.

(21) Appl. No.: 12/241,432

(22) Filed: Sep. 30, 2008

(65) Prior Publication Data

US 2010/0077828 A1  Apr. 1, 2010

(51) Int. Cl.
*G01N 1/22* (2006.01)
(52) U.S. Cl. ........................................ 73/19.12
(58) Field of Classification Search .................. 73/19.1, 73/863.21, 31.01
See application file for complete search history.

(56) References Cited

U.S. PATENT DOCUMENTS

| | | | |
|---|---|---|---|
| 3,410,780 A * | 11/1968 | Holden | 204/422 |
| 5,749,942 A | 5/1998 | Mattis et al. | |
| 2003/0029228 A1 | 2/2003 | Bloder et al. | |
| 2004/0261500 A1 | 12/2004 | Ng et al. | |
| 2005/0086998 A1 | 4/2005 | Qin | |
| 2005/0241382 A1 | 11/2005 | Coenen | |
| 2007/0068493 A1 | 3/2007 | Pavlovsky | |
| 2007/0125153 A1 | 6/2007 | Visel et al. | |
| 2007/0240491 A1 | 10/2007 | Pavlovsky et al. | |

FOREIGN PATENT DOCUMENTS

| | | | |
|---|---|---|---|
| JP | 62-249045 A | 10/1987 | |
| JP | 2004279063 A | 10/2004 | |

OTHER PUBLICATIONS

Cargol, Tim, "An Overview of Online Oil Monitoring Technologies", Weidmann-ACTI, Inc., Fourth Annual Weidmann-ACTI Technical Conference, San Antonio, 2005, pp. 1-6.
Pavlovsky et al., "Palladium Nanoparticle Hydrogen Sensor", Gases & Technology Feature Jul./Aug. 2006, pp. 18-21.
Gas and Moisture Monitor GMM, Tree Tech Sistemas Digitais, CA-029, Jul. 20, 2006 Rev.2, pp. 1-6.
GE HydranMs Sensor, Technical Specifications, Appendix A, Part 16374, Rev. 2, Jul. 2005, A-1. pp. A1 -A10.

(Continued)

*Primary Examiner* — Hezron E Williams
*Assistant Examiner* — Tamiko Bellamy
(74) *Attorney, Agent, or Firm* — Stephen B. Salai, Esq.; Paul A. Leipold, Esq.; Harter Secrest & Emery LLP

(57) ABSTRACT

The invention is directed at a method of sensing hydrogen gas in a liquid comprising: providing a measuring device comprising a hydrogen sensing chamber and a palladium hydrogen sensor mounted in contact with said chamber, positioning a hydrogen permeable membrane between the liquid and the hydrogen sensor and creating a headspace, selectively providing air to the sensor headspace, thereby bringing air into contact with said palladium sensor to refresh the palladium, after the palladium sensor is refreshed shutting off air flow to the sensor headspace, bringing liquid into said chamber, allowing hydrogen to pass through the membrane and reach equilibrium, and reading the hydrogen concentration.

28 Claims, 19 Drawing Sheets

OTHER PUBLICATIONS

Calisto, Dissolved Hydrogen and Water Monitor, Morgan Schaffer Systems, Transformers—The Inside View, Jun. 20, 2007.
PCT—Notification of Transmittal of the International Search Report and the Written Opinion of the International Searching Authority, or the Declaration; dated Mar. 11, 2010 (in corresponding International Application No. PCT/US2009/054151) (4 pages).
PCT—International Search Report in corresponding International Application No. PCT/US2009/054151; dated Mar. 11, 2010 (3 pages).
PCT—Written Opinion of the International Searching Authority in corresponding International Application No. PCT/US2009/054151; dated Mar. 11, 2010 (4 pages).

* cited by examiner

SECTION A-A

SECTION B-B

SECTION C-C

SECTION D-D

SECTION E-E

SECTION A-A

SECTION B-B

SECTION C-C

SECTION D-D

SECTION E-E

US 8,028,561 B2

HYDROGEN SENSOR WITH AIR ACCESS

BACKGROUND OF THE INVENTION

1. Field of the Invention

This invention relates to measurement of hydrogen gas in a liquid. It particularly relates to the measurement of hydrogen gas in oil.

2. Description of Prior Art

The measurement of hydrogen gas in the oil of an electrical transformer is of interest as it is an indication of the breakdown of the oil caused by overheating and/or arcing inside the transformer. Transformer oil cools the transformer and acts as a dielectric. As transformer oil ages it becomes a less effective dielectric. The increase in hydrogen dissolved in the transformer oil is an indicator of the coming failure of the transformer.

There is also need for determining hydrogen concentration in the oil of long-running engines such as those utilized in electric generation and powering ships. The monitoring of hydrogen level in cooking oils also would be useful to determine when to change the oil. The monitoring of hydrogen content of oil in hydrogen powered engines is also of interest.

For large transformers there are hydrogen sensors that use gas chromatography or photo-acoustic spectroscopy to determine the amount of hydrogen gas within a transformer's oil. Such devices are very expensive and the expense is not justified for smaller transformers. There are many older, small transformers that could be monitored if a low-cost method of doing so was available.

A lower-cost gas monitor, the Hydran™ M2 manufactured by General Electric Company has been in use. However, this gas monitor only senses combustible gases and then uses a formula to estimate how much of the gas typically is hydrogen and how much is other gases.

An article "Overview of Online Oil Monitoring Technologies" by Tim Cargol at the Fourth Annual Weidmann—ACTI Technical Conference, San Antonio 2005 provides a discussion of oil gas measuring techniques, including hydrogen measurement.

Palladium hydrogen sensors are disclosed in Gases and Technology, July/August 2006, in the article, "Palladium Nanoparticle Hydrogen Sensor" pages 18-21. Palladium sensors are also disclosed in US patent publications US 2007/0125153-Visel et al., US 2007/0068493-Pavlovsky, US 2004/0261500-Ng et al.

There's a need for low-cost method of determining hydrogen gas content in oils, such as in transformers and long-running engines, and other liquids such as organic cooling liquids, such as glycols, and also for cutting coolant liquids used in cooling of metal cutting devices.

BRIEF SUMMARY OF THE INVENTION

This invention is directed to a method of sensing hydrogen gas in a liquid comprising: providing a measuring device comprising a hydrogen sensing chamber and a palladium hydrogen sensor mounted in contact with said chamber, positioning a hydrogen permeable membrane between the liquid and the hydrogen sensor and creating a headspace between the sensor and the membrane, selectively providing air to the sensor headspace, thereby bringing air into contact with said palladium sensor to refresh the palladium, after the palladium sensor is refreshed shutting off air flow to the sensor headspace, bringing liquid into said chamber, allowing hydrogen to pass through the membrane and reach equilibrium, and reading the hydrogen concentration from the sensor.

BRIEF DESCRIPTION OF THE SEVERAL VIEWS OF THE DRAWING(S)

Figure 16:
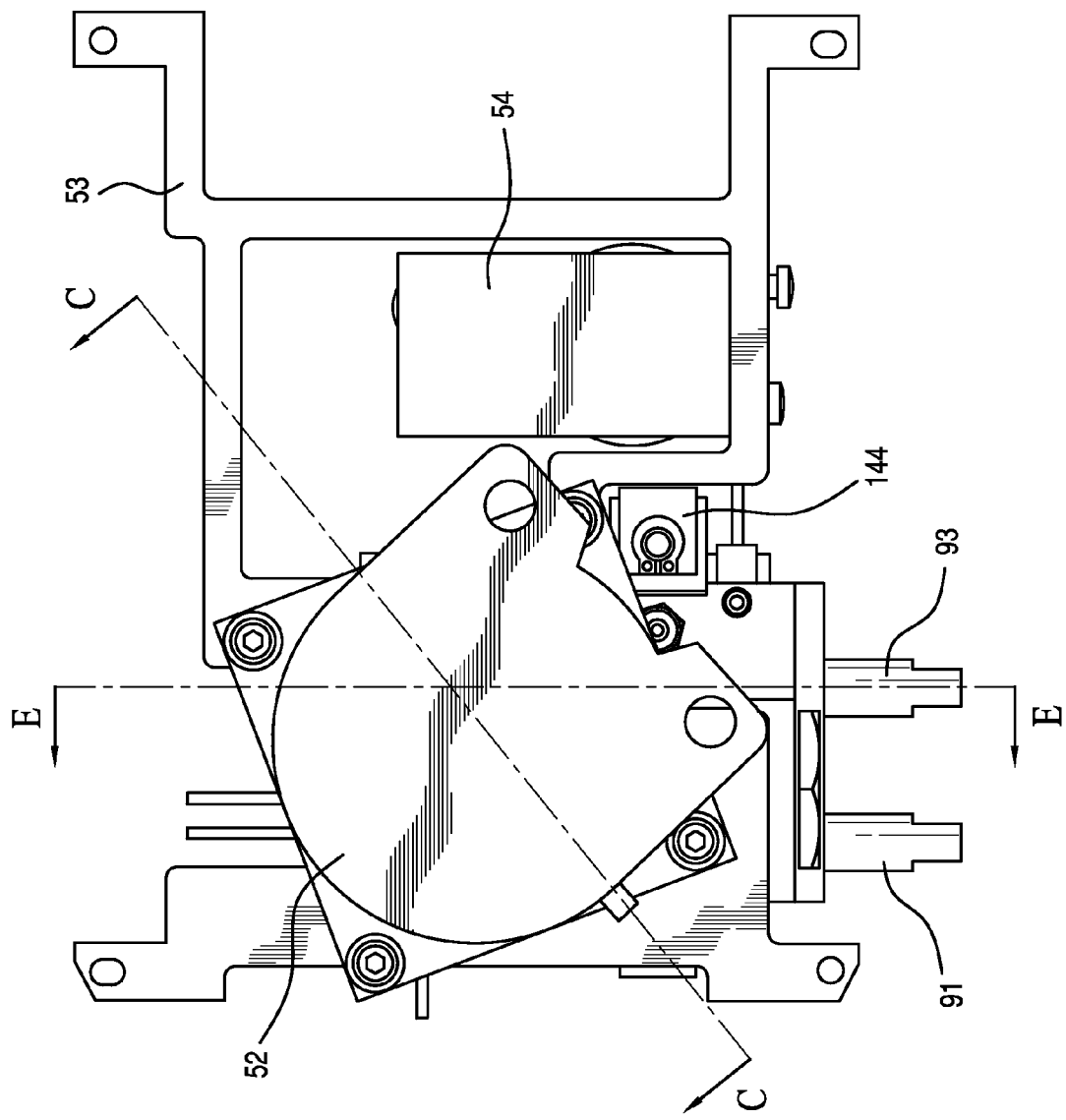
Figure 17:
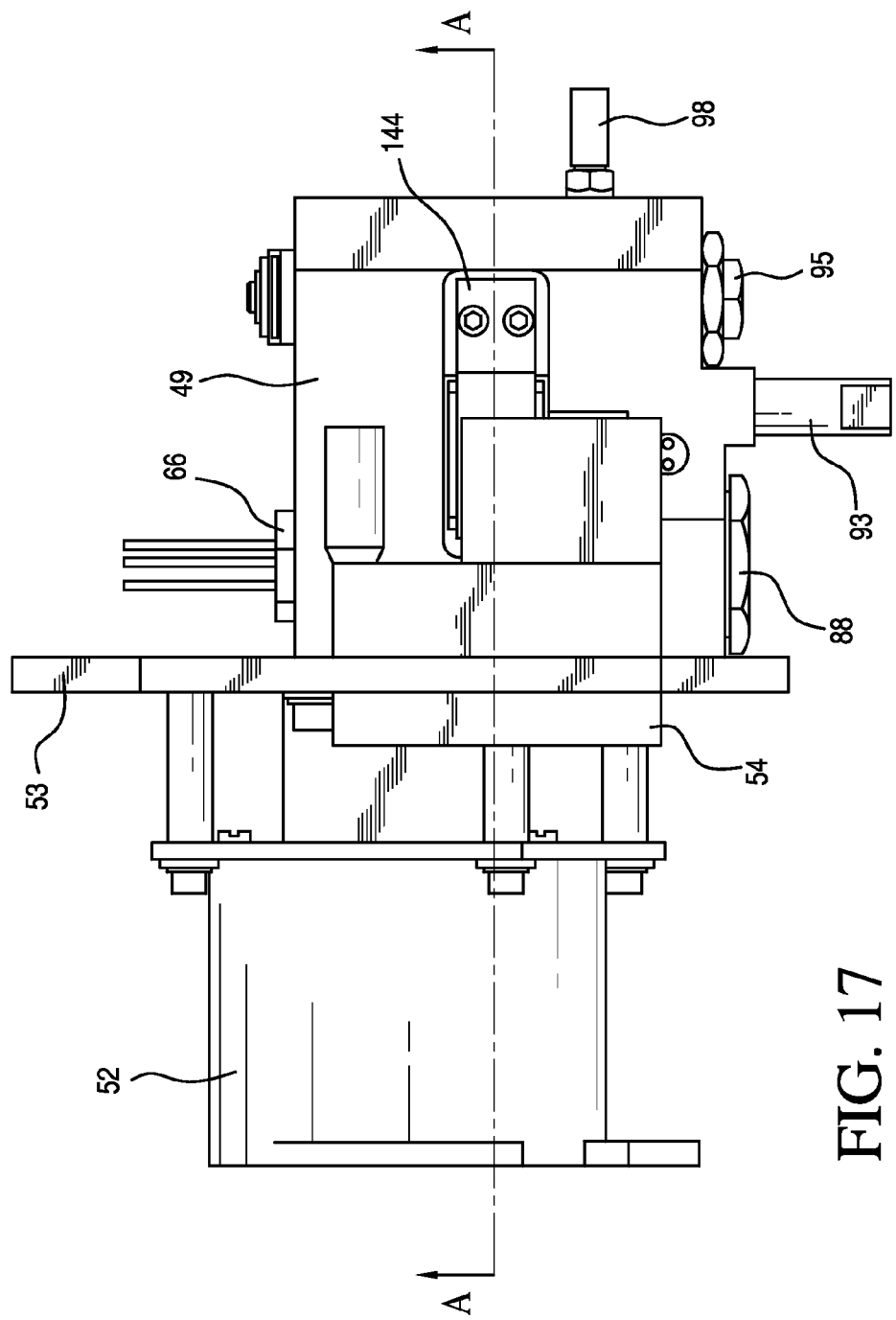
Figure 18:
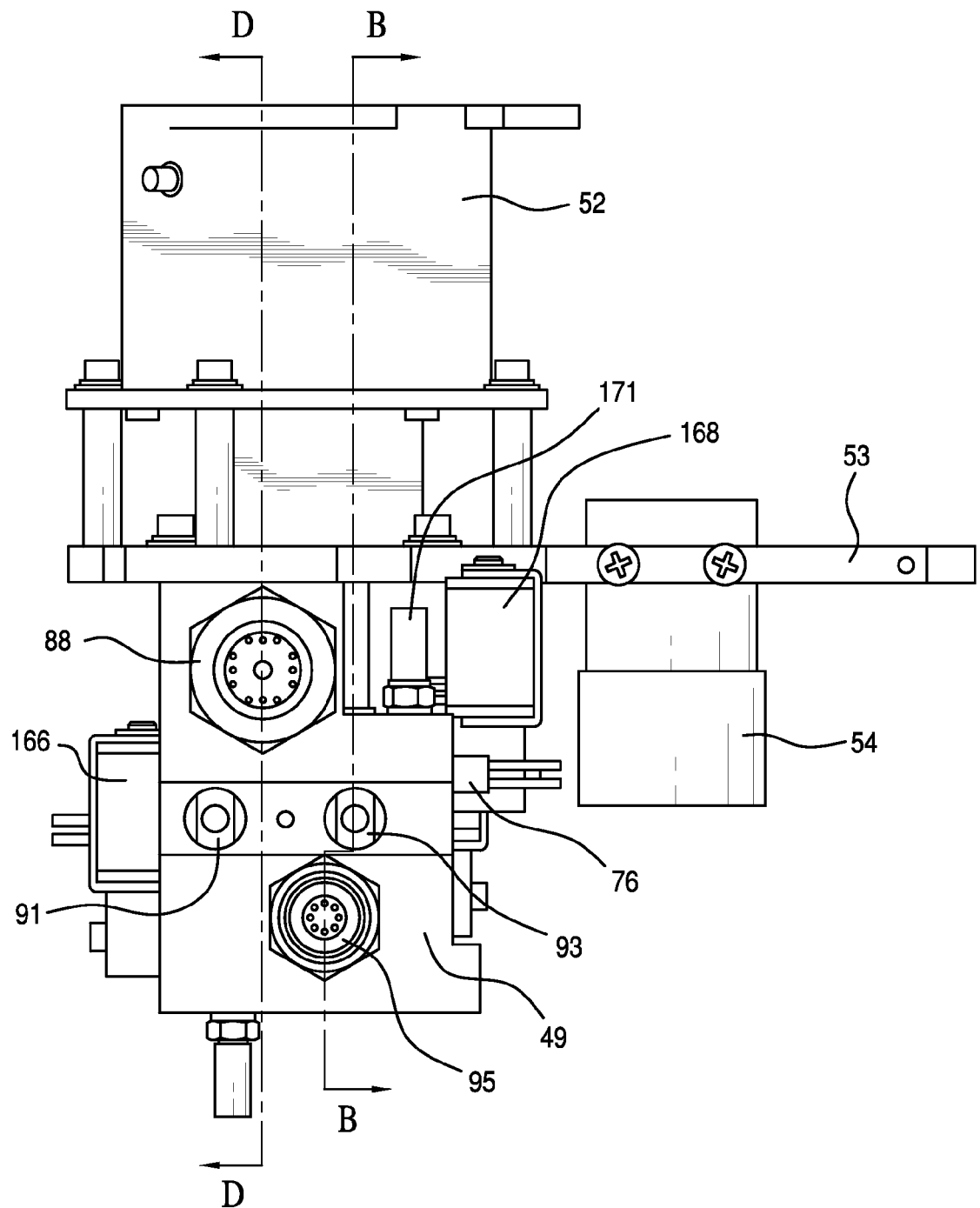

FIGS. 16, 17, and 18 are views of another embodiment of the invention with section lines indicated.

Figure 19:
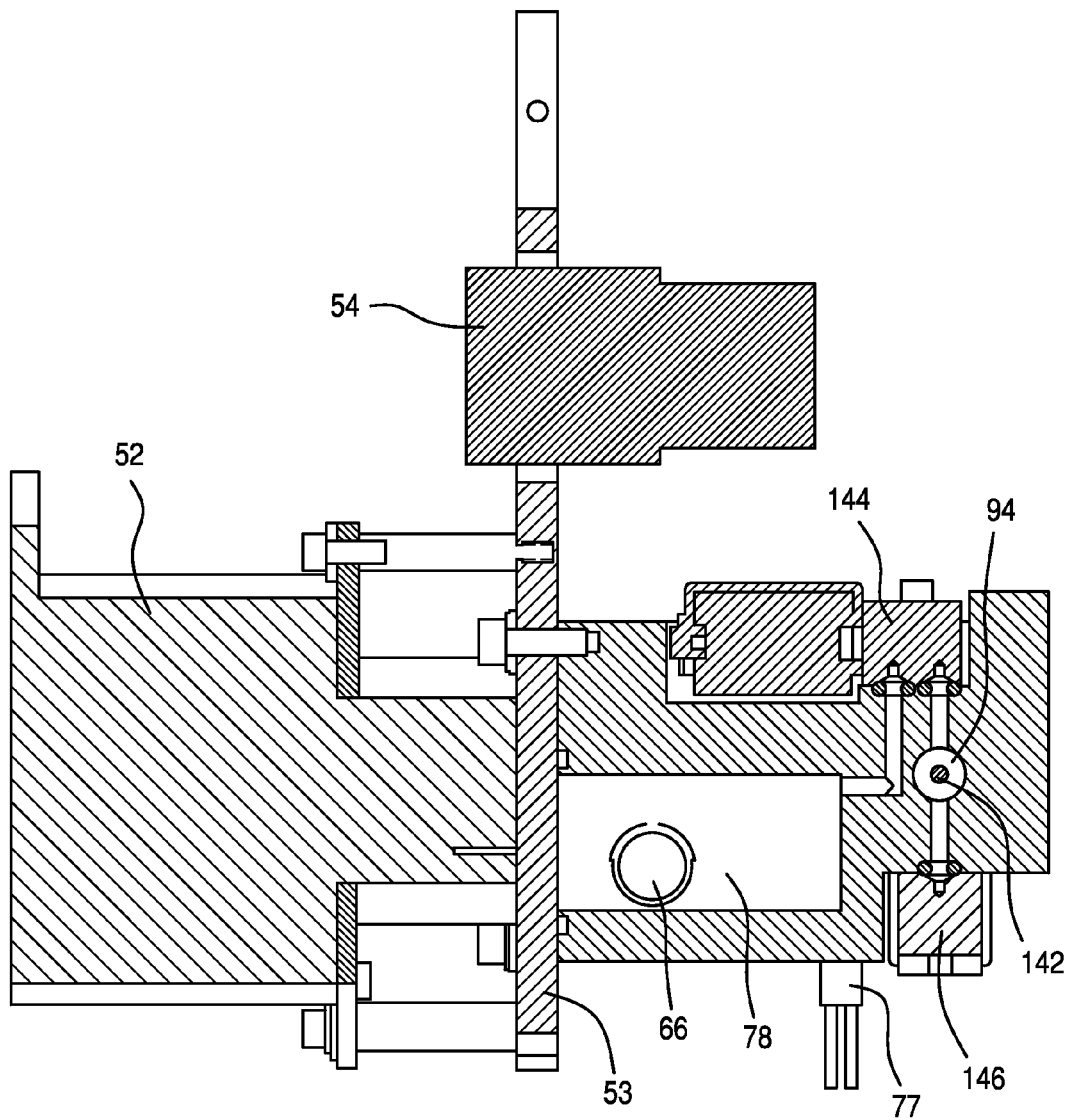

FIG. 19 is a cross-section on line A-A of FIG. 17.

Figure 20:
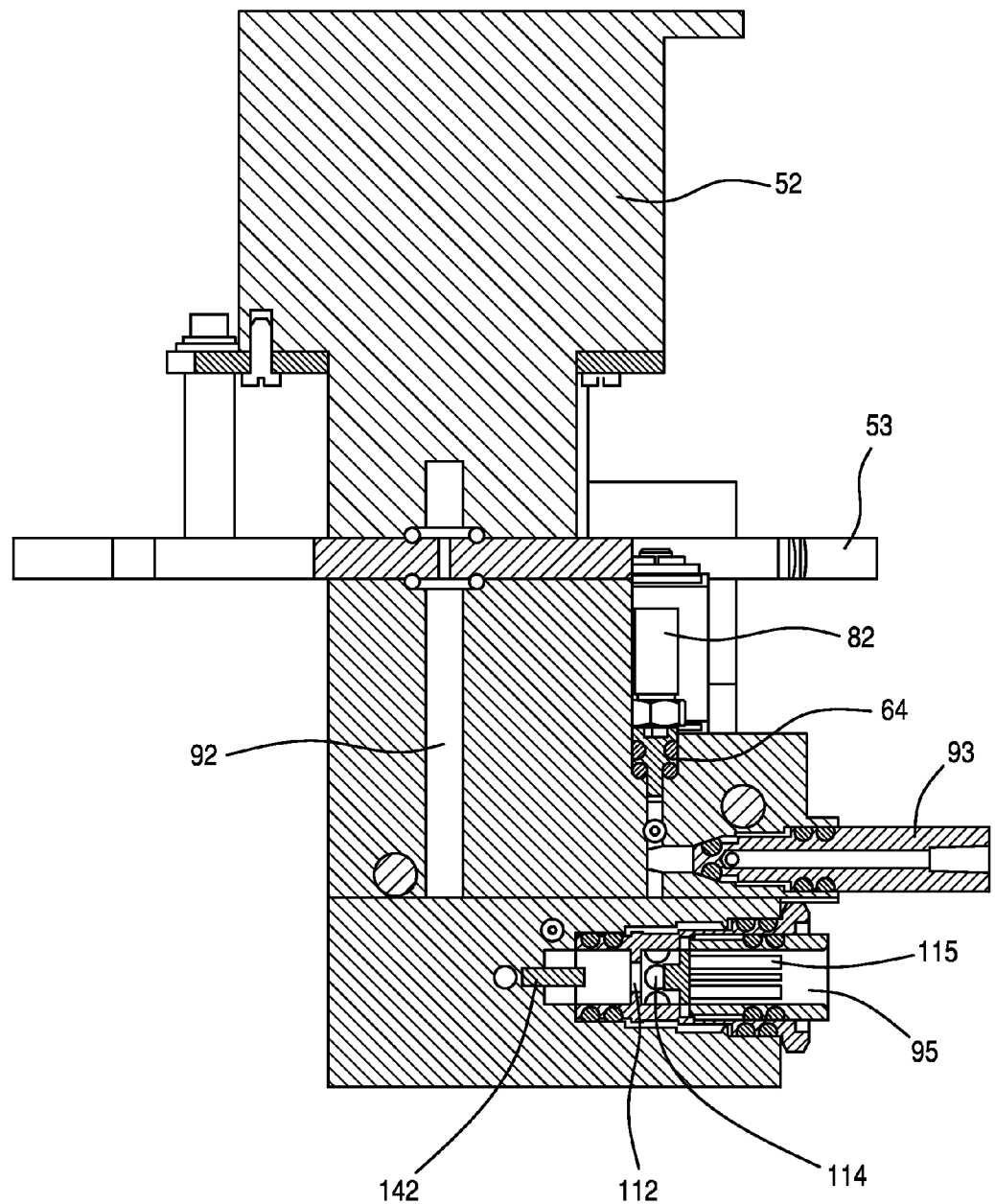

FIG. 20 is a cross-section on line B-B of FIG. 18.

Figure 21:
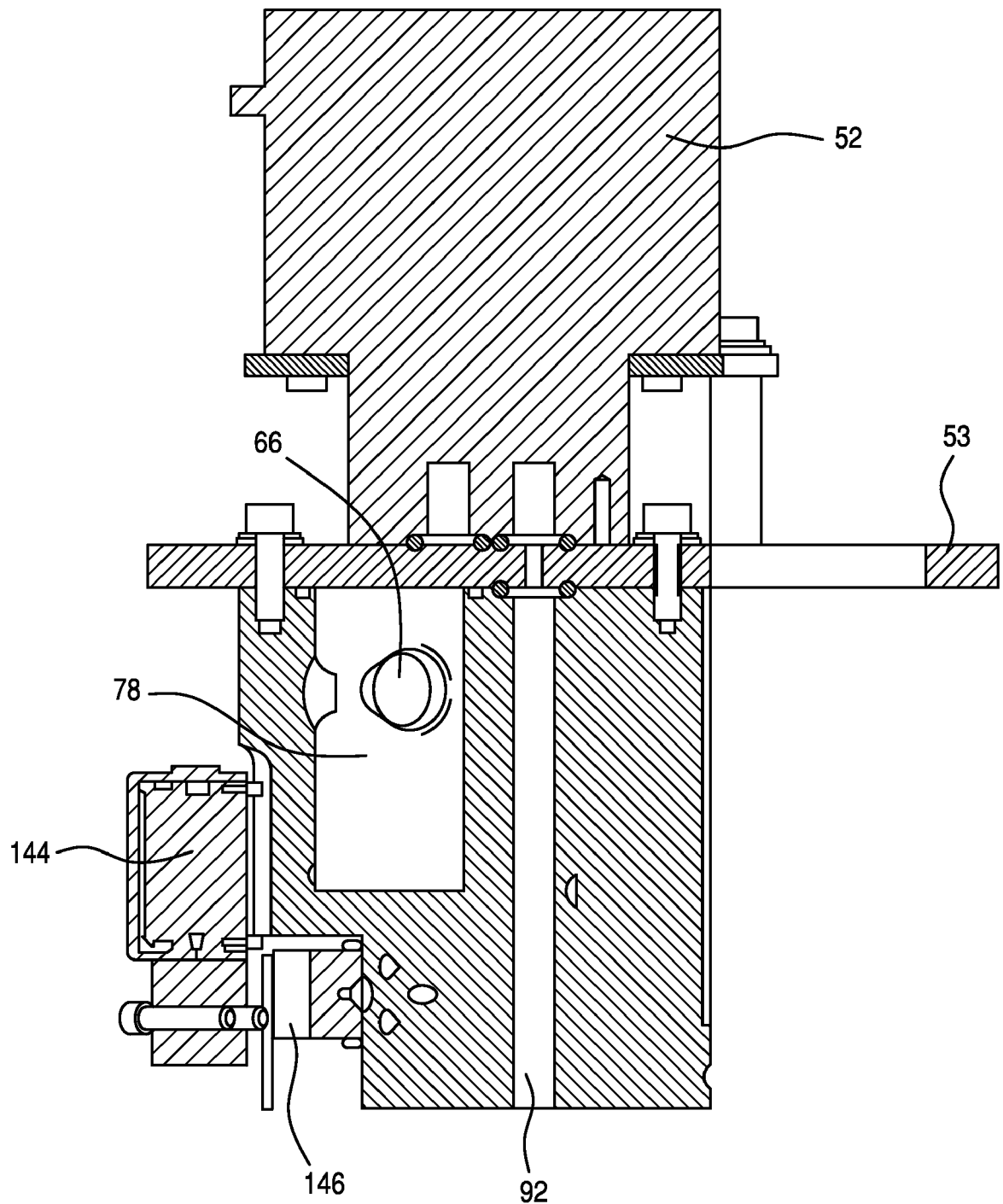

FIG. 21, is a cross-section on C-C of FIG. 16.

Figure 22:
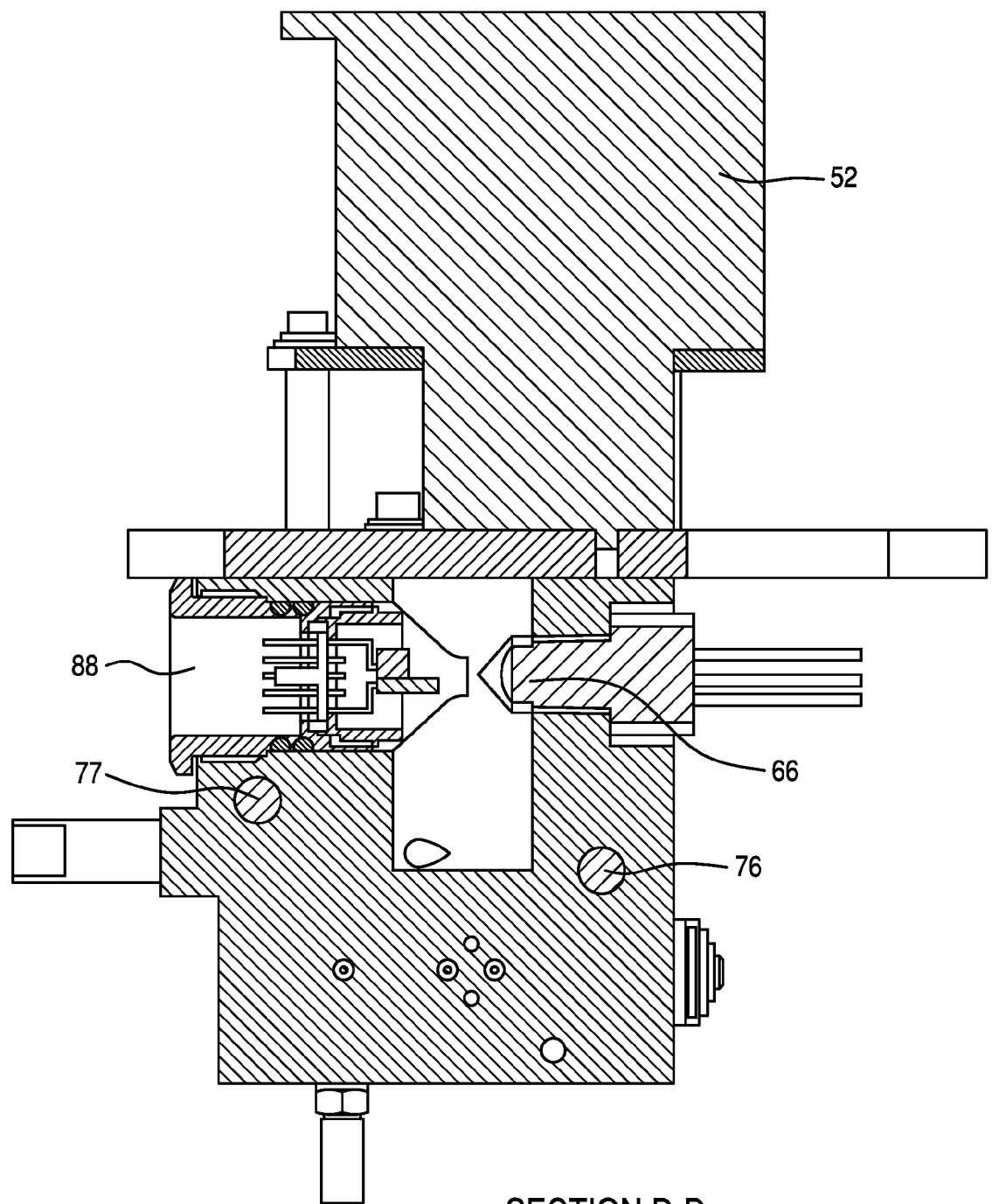

FIG. 22 is a cross-section on D-D of FIG. 18.

Figure 23:
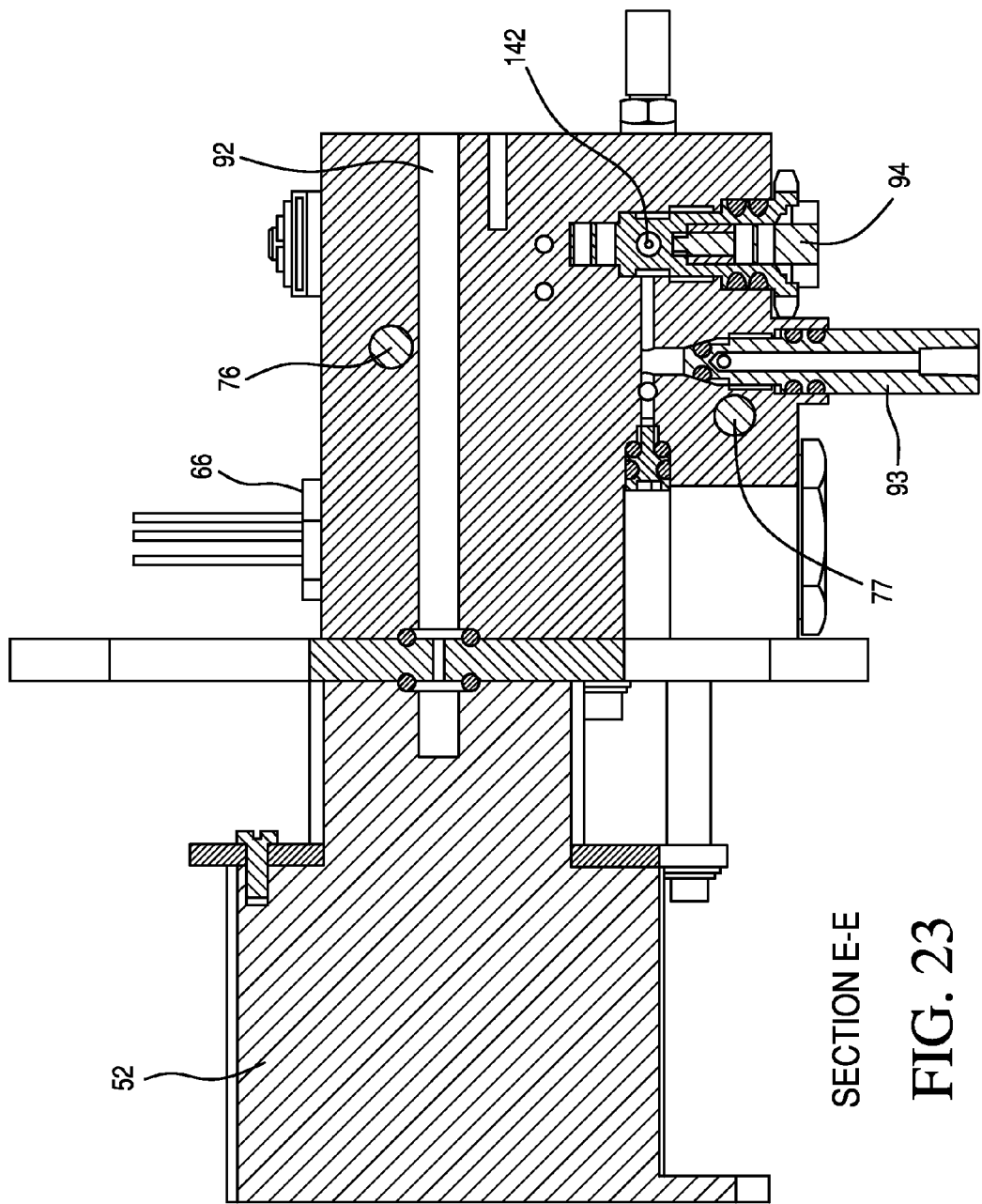

FIG. 23 is a section online E-E of FIG. 16.

Figure 24:
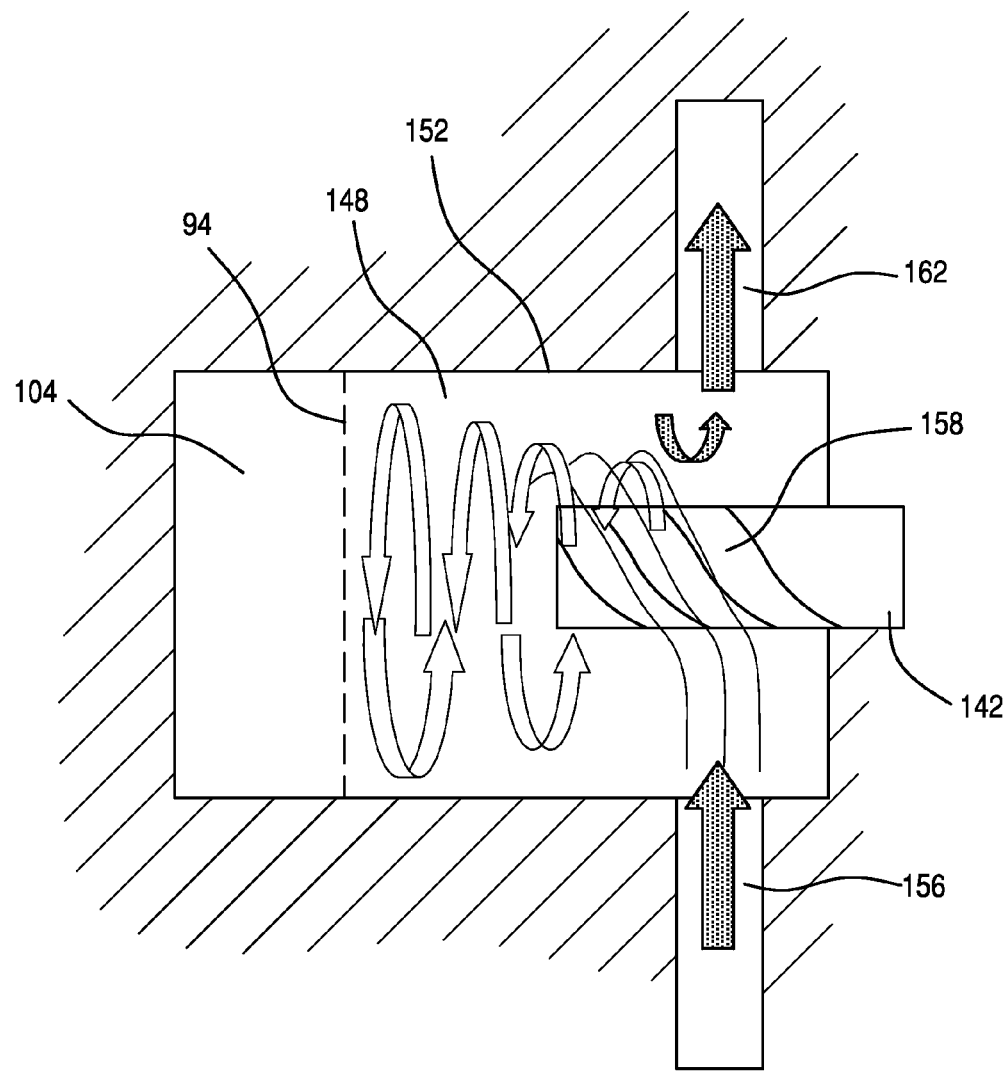

FIG. 24 is a cross-section of the vortex generator in the hydrogen measuring chamber.

Figure 25:
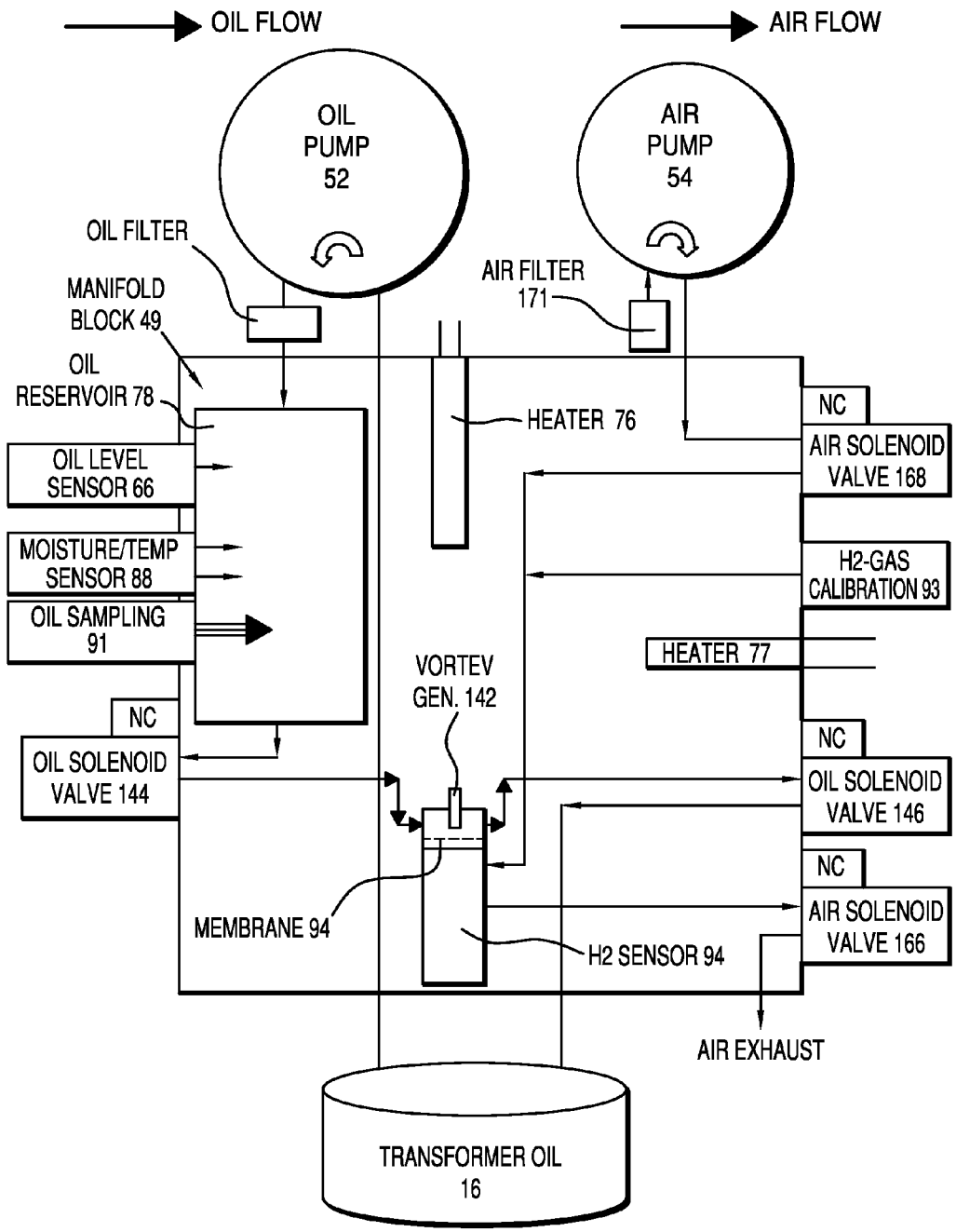

FIG. 25 is a schematic of the apparatus and method of the invention showing the flow of oil and air through the device for measurement of hydrogen, moisture and temperature.

DETAILED DESCRIPTION OF THE INVENTION

The invention provides numerous advantages over prior apparatus and methods. The invention is smaller and lower in cost than other hydrogen sensing devices. The device is accurate and can be easily retrofitted onto existing tanks or engines. The device provides a very accurate hydrogen sensor as well as a system for maintaining the accuracy of the hydrogen sensor. The device provides a method for moving the liquid, such as oil, across or around the sensor so as to obtain accurate readings. The device allows replacement of the sensor without providing an opening for oil to leave the container. The invention sensor utilizes instrument controls that are well-known and available. These and other advantages will be apparent from the description below.

Figure 1:
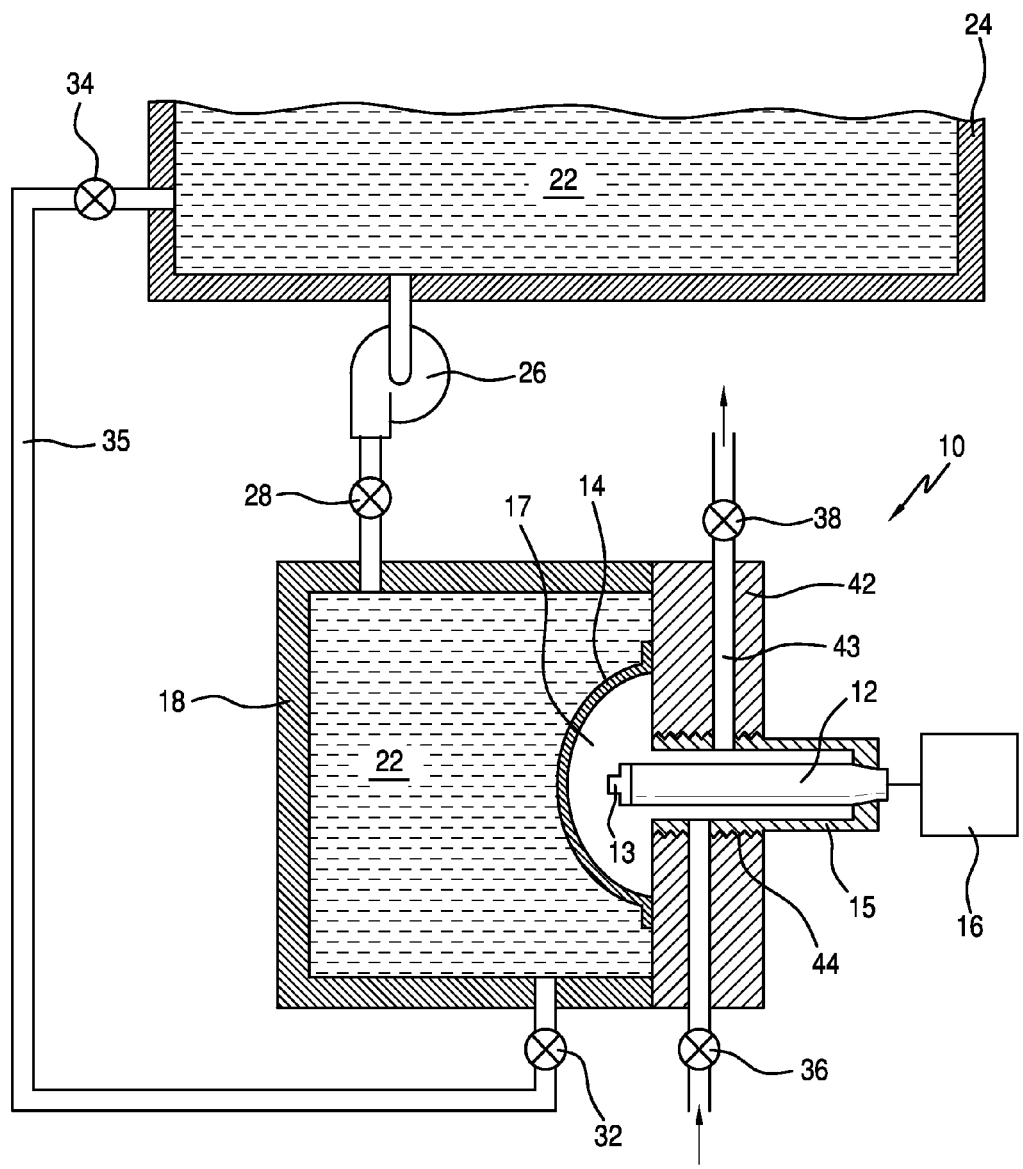
FIG. 1 is a schematic view of an apparatus for measuring hydrogen content in a test container connected to a large liquid container.
Figure 2:
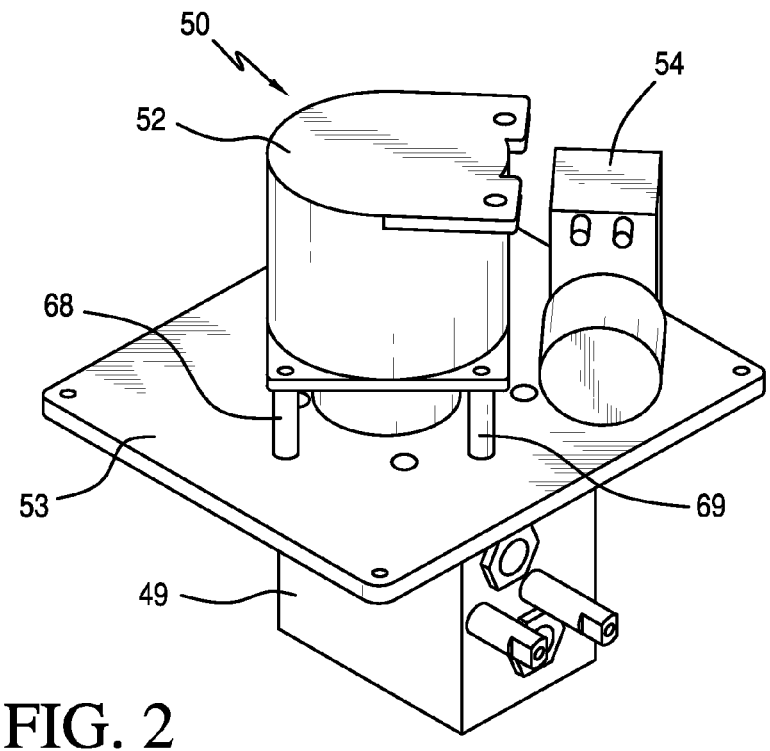
FIGS. 2-6 are perspective views of a device for a hydrogen gas measurement.

FIG. 1 shows apparatus 10 for hydrogen measurement. The apparatus comprises hydrogen sensor 12, hydrogen permeable membrane 14, controller 16, and oil test container 18. In operation the liquid, typically oil 22, enters from container 24 into test container 18. The liquid flow is controlled by a pump 26. The flow of oil is also controlled by valve 28 for entry of oil into the test unit 18, and valves 32 and 34 for exit of the oil from the test container 18 and return to the container 24 through pipe 35. The oil typically would flow past the membrane 14 prior to isolation of container 18 for testing in order to obtain a valid average sample contained in test container 18 from the large container 22. The membrane 14 typically would be formed from the material such as a PTFE fabric that would be permeable to hydrogen, allowing passage of hydrogen and other gases through the membrane into headspace 17 without allowing oil to pass. The hydrogen sensor 12 is mounted in casing 15 screwed with threads 44 into the side 42 of test container 18. Prior to testing the amount of hydrogen in the fluid the hydrogen sensor 12 having a palladium tip 13 would be subject to a flow in headspace 17 of air or other oxygen containing gas that enters through valve 36 and exits through valve 38. The flow of gas would be carried out for sufficient time to renew the palladium 13 and purge any hydrogen remaining from the previous samples such that accurate hydrogen testing may be carried out. After sufficient time, typically between 1 and 2 minutes the palladium is renewed and valves 36 and 38 are closed creating a gas tight gaseous headspace 17 around the sensor 12. After the sensor has been isolated by closing valves 38 and 36, the gas headspace 17 is allowed to reach equilibrium and hydrogen readings are taken by sensor 12 and processed by controller 16 to give hydrogen content in the oil. The time to reach equilibrium so a reading can be taken typically is between 2 and 6 hours. While the drawing of FIG. 1 indicates that the air is supplied by ducts 43 in the wall 42 of the test container, it is also possible that air inlets could be provided in casing 15 of the sensor 12. In the palladium hydrogen sensor 10 it is necessary to initially insert a known quantity of hydrogen gas and air into the chamber 17 through valve 36 and exit valve 38 to calibrate the sensor.

Figure 3:
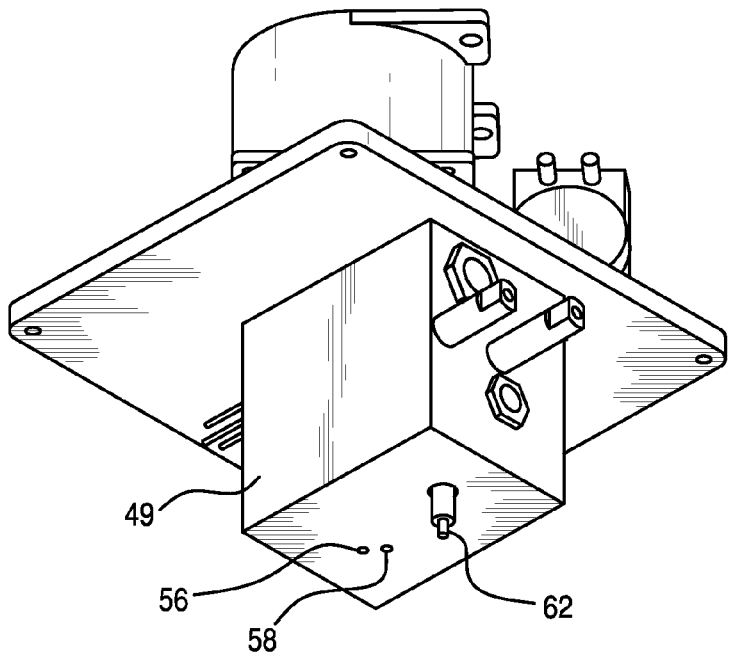
Figure 4:
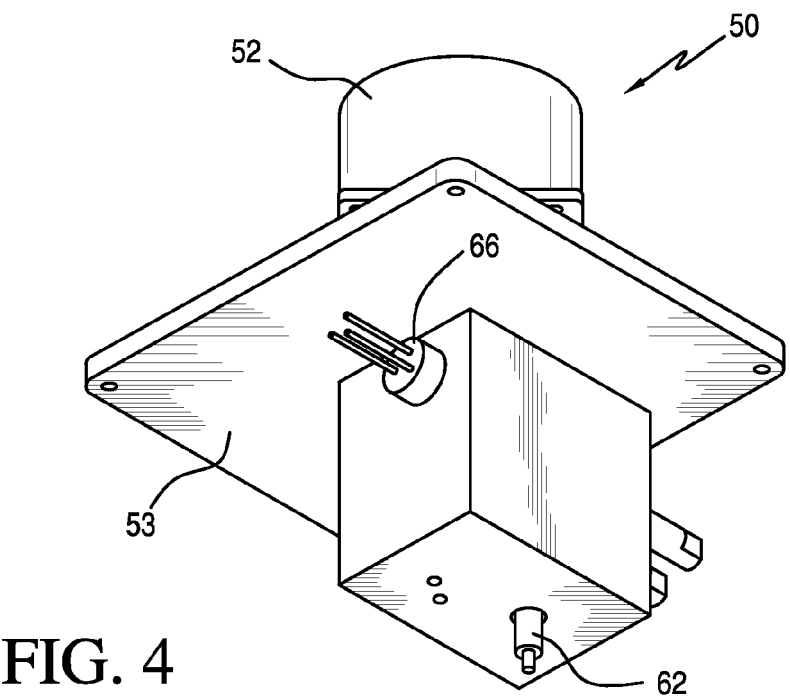
Figure 5:
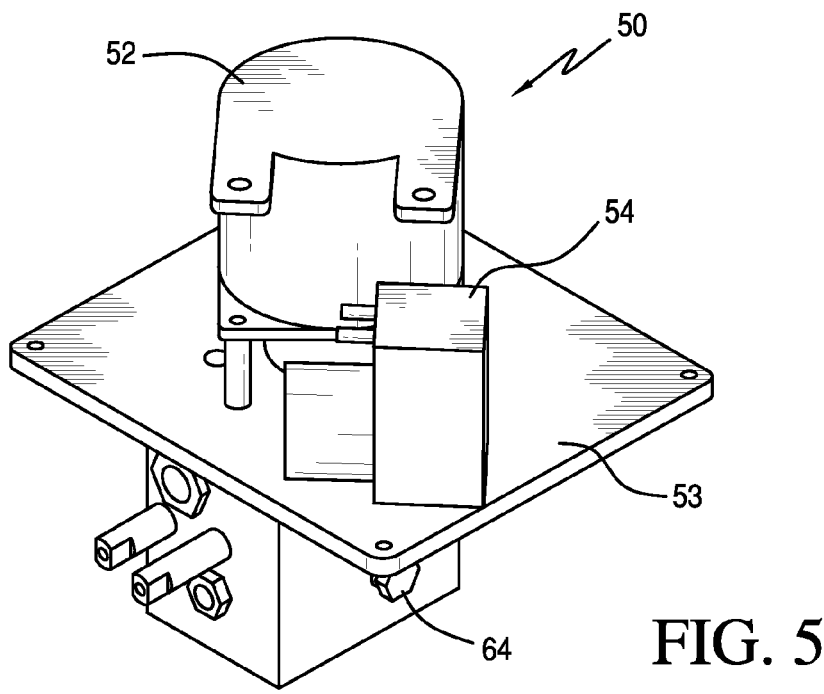
Figure 6:
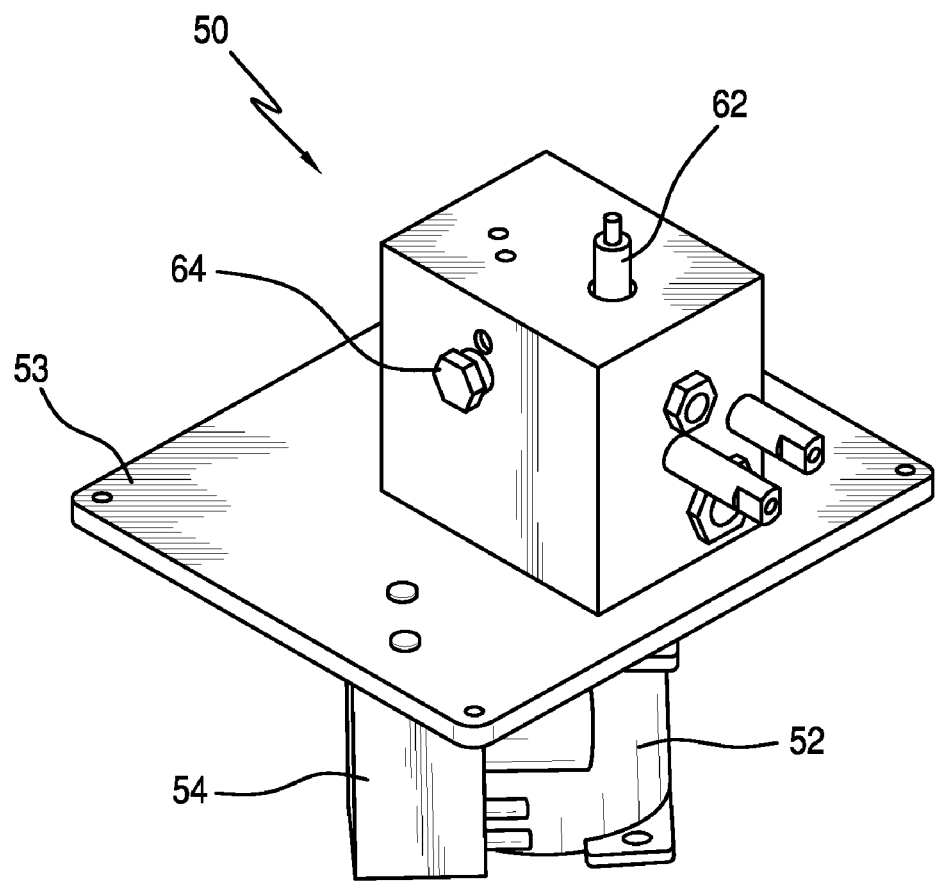

In FIGS. 2, 3, 4, 5 and 6 there are prospective views of a measuring device 50 in accordance with the invention. The device comprises a manifold block 49, oil pump 52, and air pump 54. The device 50 is provided with oil in and oil out holes 56 and 58 respectively as seen in FIG. 3. The air exit check valve 62 is visible in FIGS. 3 and 4. The measuring device is provided with a stopper 64 to plug the hole where an oil passage was drilled. The oil level sensor 66 is adapted to sense oil level in the moisture sensing compartment. The pump 52 will shut off shortly after oil is not sensed by sensor 66. The measuring device is mounted on plate 53 using attachment points 68 and 69 as well as other mounting points not shown.

Figure 7:
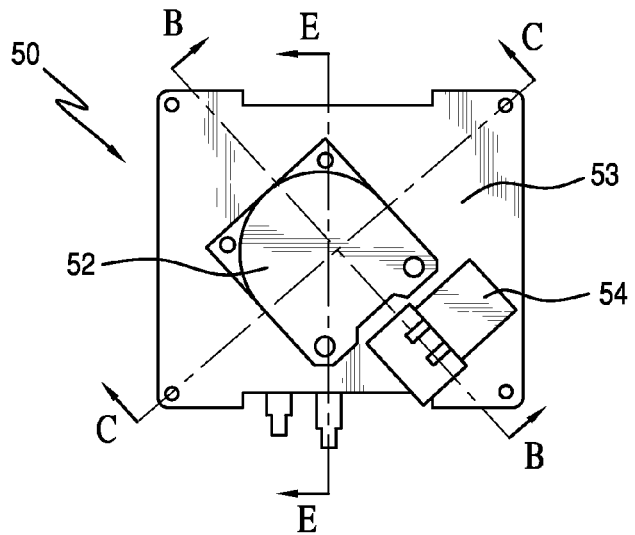
FIGS. 7-9 are top and side views of hydrogen measurement device of the invention indicating the section lines A-A, B-B, C-C, D-D, and E-E.
Figure 8:
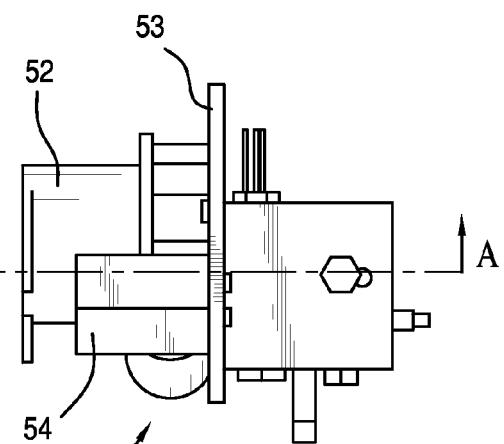
Figure 9:
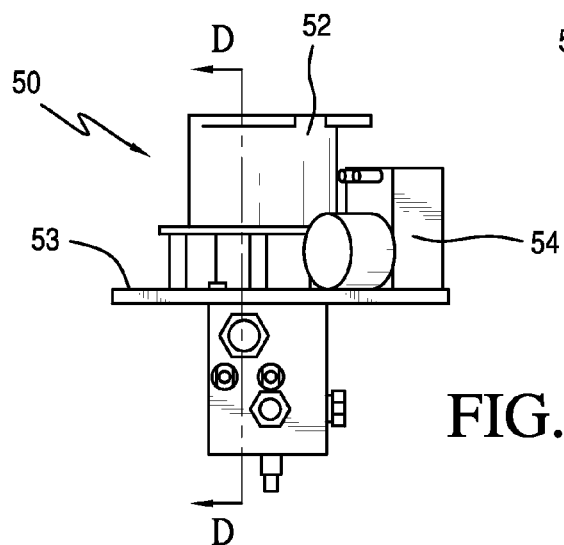

FIGS. 7, 8, and 9 are a top and two side views of the measuring device 50 of the invention. FIG. 7 shows cross-section lines B-B, C-C, and E-E. FIG. 8 shows cross-section line A-A. FIG. 9 shows cross-section line D-D.

Figure 10:
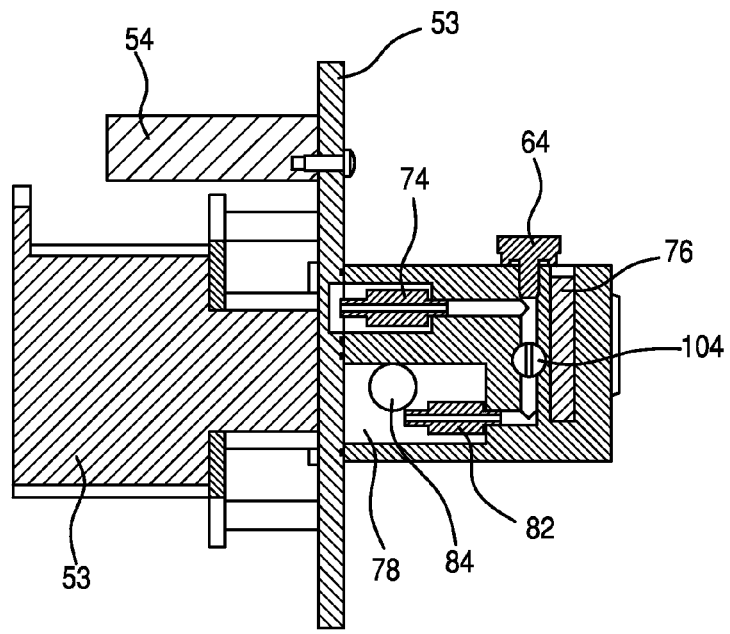
FIG. 10 is the view on section line A-A of FIG. 8.

FIG. 10 shows the measuring device as seen on section A-A of FIG. 8. In FIG. 10 there is shown a hydrogen sensing chamber 104 and a check valve 74 controlling oil flow from the chamber. Heater 76 provides heat to maintain the measuring device at a stable temperature during measurement so that the results taken at different times are comparable and to provide for the best functioning of the hydrogen detector. The measuring device also has a moisture sensing compartment 78 that is provided with oil shutoff valve 82 and oil level sensor 84.

Figure 11:
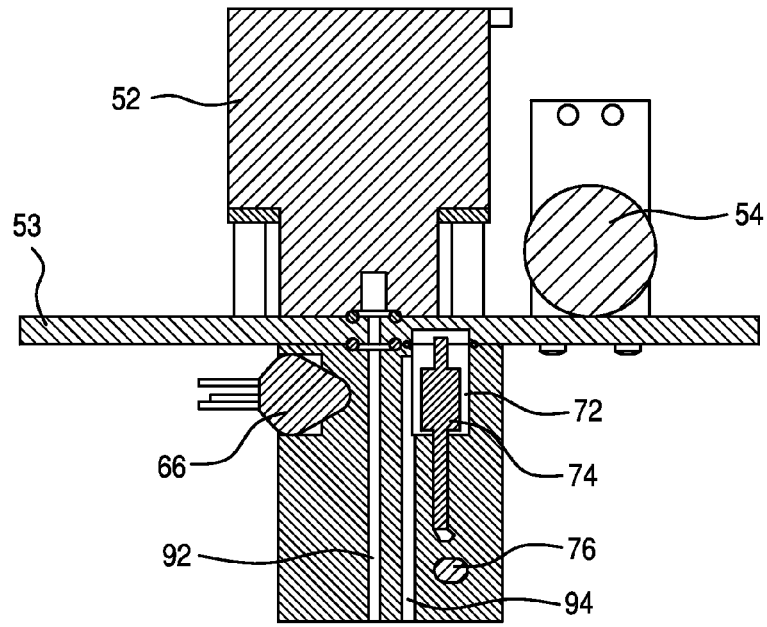
FIG. 11 is a view on section line B-B of FIG. 7.

FIG. 11 which is on section line B-B of FIG. 7 shows the oil entry channel 92 and exit channel 94. Also shown are the wiring terminals 66 for oil level sensor 84.

Figure 12:
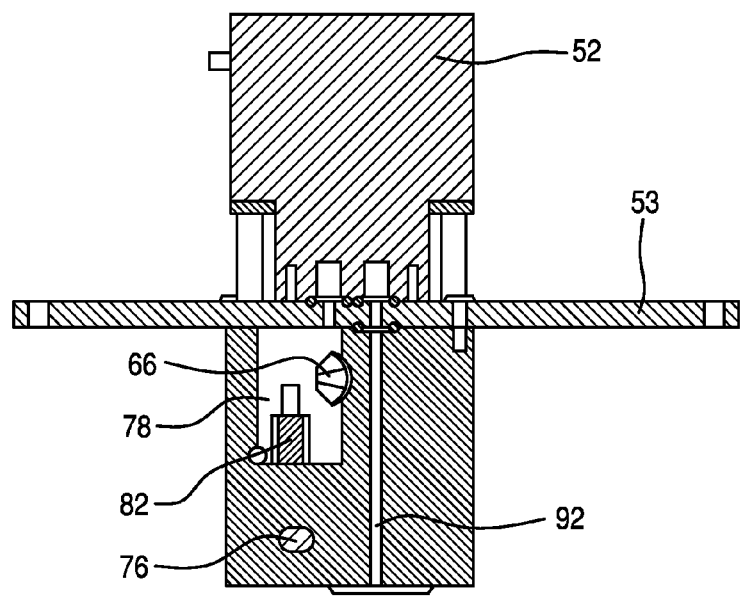
FIG. 12 is a view on section line C-C of FIG. 7.
Figure 13:
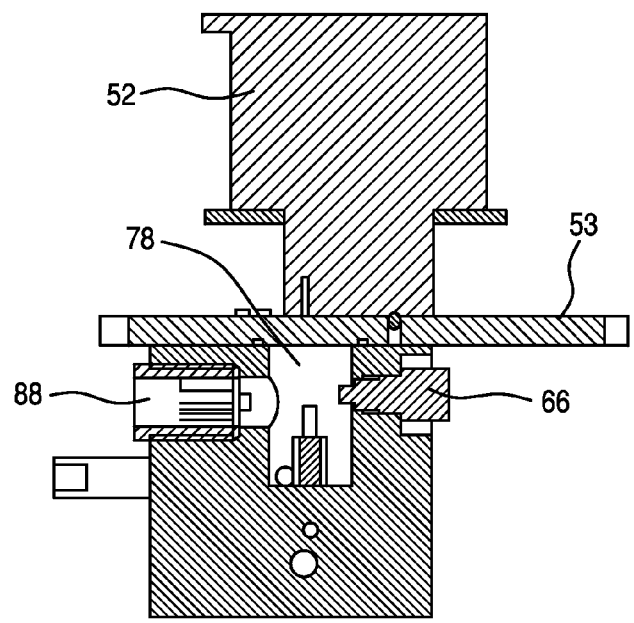
FIG. 13 is a view on section line D-D of FIG. 9.

FIG. 12 shows a section of device 50 taken on cross-section on line C-C of FIG. 7. The moisture sensor compartment 78 is shown with oil level sensor 66. In FIG. 13 which is on section line D-D of FIG. 9 is shown the moisture sensing chamber 78 with moisture sensor 88 and the oil level detector 66. The moisture detector 88 detects the moisture present in the oil of a transformer or other device, not shown, and also contains a temperature sensor for temperature control and percent moisture calculations.

Figure 14:
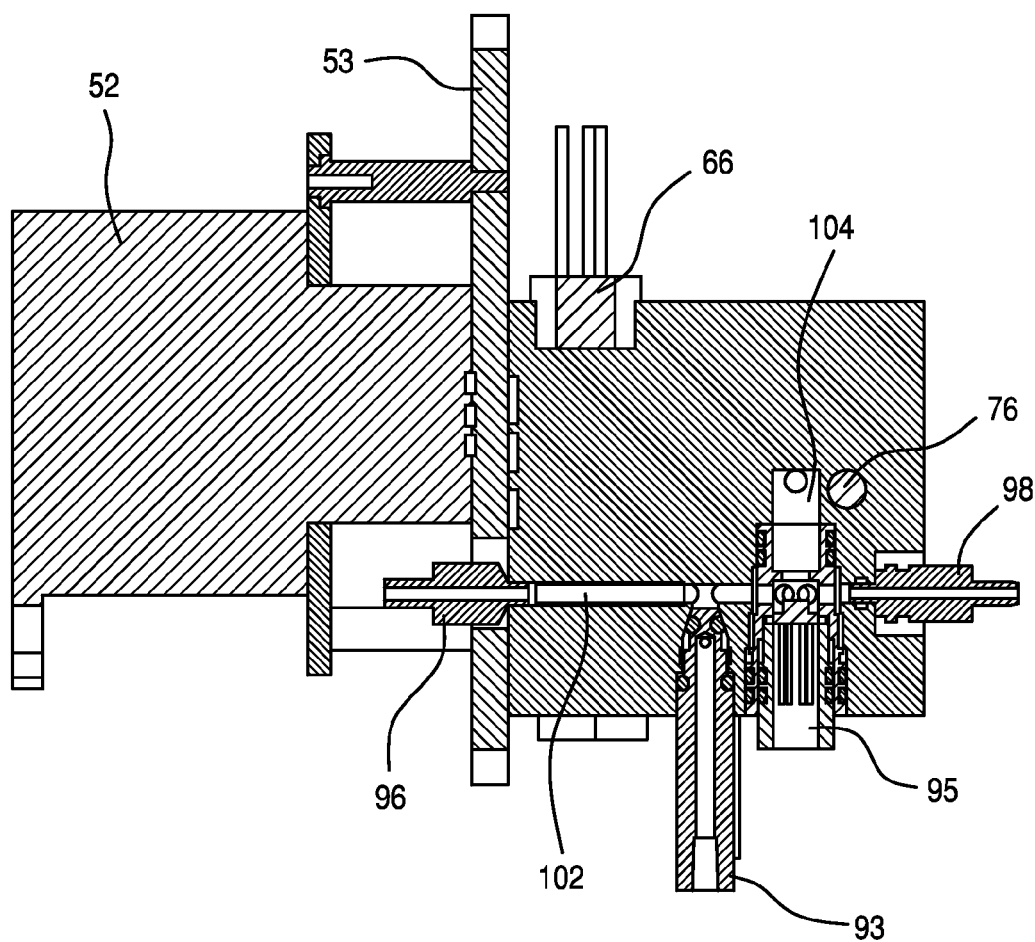
FIG. 14 is a view on section line E-E of FIG. 7.

In FIG. 14, taken on section line B-B from FIG. 7 is illustrated the air path used for refreshing the palladium of the hydrogen sensor. The air path 102 is controlled by valves 96 and 98 and allows the passage of air into air path 102 and into contact with the palladium to refresh it for accurate hydrogen measurement. The hydrogen measurement device 95 is in contact with the oil hydrogen sensing chamber 104. The calibration injection port 93 allows the injection of known hydrogen containing gas sample into contact with the palladium of the hydrogen sensor in order to determine and calibrate the accurate operation of the sensor, and also allows for the withdrawal of gas samples for external analysis.

Figure 15:
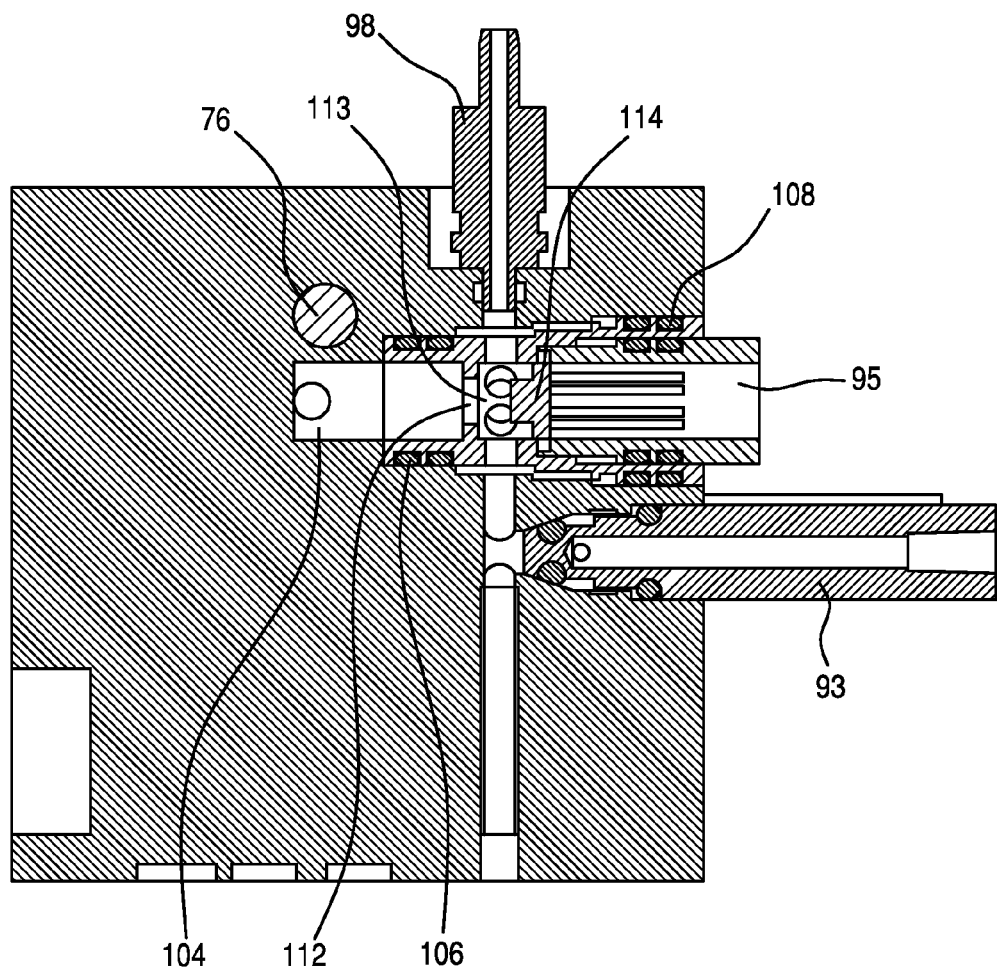
FIG. 15 is an enlargement of the section of FIG. 14 showing the hydrogen sensor in detail.

FIG. 15 is an enlargement of a section of FIG. 14 showing hydrogen sensor 95 in more detail. The hydrogen sensor 95 extends into the hydrogen sensing chamber 104. The sensor 95 is provided with sealing rings 106 and 108 to isolate the sensor from oil and air. The sensor 95 is provided with a membrane 112, typically Teflon, that is microporous and will allow the passage of hydrogen from the oil in the hydrogen sensing chamber 104 into contact with the palladium 114 of the sensor and not allow the passage of oil. The hydrogen sensor is provided with electrical leads 115 to allow the connection of the sensor to the controller, not shown.

As shown in FIGS. 2-15 in operation of the sensor of the invention air pump 54 passes air through air inlet 96 and out of air outlet 98. Pump 52 circulates the oil by drawing oil through channel 92 from a source, such as a transformer, (not shown) through channel 92 and then fills the hydrogen sensing chamber 104 through entry valve 82 such that oil fills the reservoir 102 and continually exits through outlet 74 for return to the oil source. The air flow from pump 54 is interrupted by closing both air inlet valve 96 and air outlet valve 98. The palladium sensor is then allowed to stabilize for about 1 minute and then air flow stopped. Prior to initial operation, airflow to the inlet 96 is stopped, and hydrogen test gas is inserted through calibration port 93. The outlet 98 is closed and then the hydrogen sensor 94 is confirmed to be in calibration. The hydrogen sensor is then refreshed by again passing air over the palladium sensor for a period of about 1 minute. Airflow is stopped, the air inlet 96 and air outlet 98 are closed, closing off headspace chamber 113 around palladium 114 of sensor 95. Oil flow through chamber 102 is stopped by oil valves 74 and 82 so that chamber 102 is isolated. A period of time, sufficient for hydrogen gas to pass through membrane 112 and reach equilibrium in the headspace 113, is allowed to pass, typically about 4 hours and then a reading is taken by the hydrogen sensor 95. It is noted that calibration of the sensor typically is required only after several years of operation. An advantage of the invention sensor system is that fresh oil is periodically pumped into the sensing chamber 104, thereby providing a more accurate reading than would be the case if the oil adjacent the semi permeable membrane was not refreshed by moving from the transformer or other oil source.

Readings from a temperature sensor and/or moisture sensor 88 may be taken at the time of hydrogen measurement or separately. The sampling of oil through a sampling valve may be carried out if one is provided on the measuring device. It would be particularly desirable to do further tests if the hydrogen measurement is elevated from previous levels. As stated above a fresh oil sample is pumped into the chamber prior to each reading.

Palladium containing hydrogen sensors and controllers for the sensors are known in the art. Such sensors are disclosed in United States patent application publications US 2007/0125153-Visel et al. and US 2007/0240491-Pavlovsky, hereby incorporated by reference. An article in Gases and Technology, July/August 2006 "Palladium Nanoparticle Hydrogen Sensor." by I. Pavlovsky, also contains a description of hydrogen sensors and the methods and apparatus for their use. The palladium nanoparticles utilized in these preferred sensors for the invention are intrinsically sensitive to hydrogen and sensors based on palladium nanoparticle networks do not produce false alarms in the presence of other gases. This makes them particularly desirable for use in the devices of the invention as other gases may be present when the hydrogen is sensed. Other hydrogen sensors and their controllers are disclosed in US applications 2007/0068493-Pavlovsky and US 2007/0240491-Pavlovsky et al. also incorporated by reference. The small pumps required for the small quantities of air and oil needed for the hydrogen sensor of the invention are well known. Typically these pumps are diaphragm pumps that are particularly suitable for accurately handling small quantities of liquid or gas. Temperature sensors and moisture sensors are also readily available in art.

Valves utilized in the measuring device of the invention may be any suitable type. They may be simple check valves or solenoid valves. It has been found preferable to use solenoid valves, particularly in the airstream as the check valves may not seal the hydrogen gas sufficiently for measurement.

The oil level sensor 66 is a safety device that ensures that if the sensor does not sense oil within several seconds of the pump turning on that the pump will shut off avoiding damage to the pump. The heaters in the measuring device generally maintain a temperature of about 800 centigrade as this allows optimum operation of the hydrogen sensor and a more predictable calculation of dissolved gas in the oil. There are preferably two heaters in the measuring device 50 shown, one heater 76 located immediately below the hydrogen measuring chamber and a second heater, not shown, parallel to the inlet 92 and outlet 94 oil channels. The use of moisture sensor to determine the moisture in the oil provides a key indicator of potential transformer problems. This is particularly useful in combination with the hydrogen level that the measuring device provides. The measuring device maintains a small chamber for the hydrogen measurement. If a large amount of oil was utilized, there would be concern that excessive oxygen migration into the oil would impair the effectiveness of the palladium sensor. As the chamber is very small with a volume of less than 1 milliliter there is a very small amount of oxygen migration possible. The preferred chamber size is between about 0.5 and 1.0 milliliters for the fastest and most accurate testing. Generally a hydrogen content reading can be taken in about 4 hours. The measuring unit generally is mounted as close as possible to the oil or other liquid container so lengthy piping will not add to oil volume.

FIGS. 16-24 illustrate a preferred embodiment of the invention. This embodiment differs from the device of FIGS. 1-15 at least in that the device contains solenoid valves and a chamber for the oil during hydrogen measurement that includes a device to form a vortex in the chamber to better mix the oil coming into the chamber with that already present and to sweep the micropermeable member in the chamber. The operation of the device is the same as the device of FIGS. 2-15. FIGS. 16, 17, and 18 are views of the device with section lines. The like parts of this embodiment are labeled with the same numbers as the parts of the previous embodiment.

In the view of FIG. 16, the oil pump 52 and air pump 54 are visible. Also shown are the oil sampling luer 91 and air sampling luer 93. The solenoid 144 for oil entering the sensor is also shown. FIG. 17 indicates the location of the hydrogen sensor 95 and oil level sensor 88. In FIG. 18, heater 91 and 93 are indicated as in air filter 171. The solenoid valves 168 for air into the sensor and 166 for air out of the sensor are indicated in FIG. 18.

In FIG. 19, a cross-section A-A of FIG. 17, there is shown oil pump 52, and air pump 54. Further, there are shown the inlet and outlet oil solenoid valves 144 and 146 respectively for bringing oil into the hydrogen measurement chamber 94 and the chamber 78 for moisture and temperature sensing.

The vortex generating member is shown at 142. In FIG. 20, a cross section B-B of FIG. 18, there is a view of the air luer 93, oil sample luer 91, and oil level sensor 66. In FIGS. 19 and 21 there is shown the oil reservoir 78 and solenoid 144. The entry passage for oil is shown in as 92. In FIG. 22, on section line D-D of FIG. 18, there is shown oil level sensor 84 and temperature and moisture sensor 88. Heaters 76 and 77 are also indicated. In FIG. 23, on section on line E-E of FIG. 16 there is shown the air luer 93 and hydrogen sensing device 94. Heaters 76 and 77 are also indicated. The pin for the vortex generator is 142.

In FIG. 24 is shown the vortex generator 142 for the oil chamber 152 where oil for hydrogen sensing is kept during hydrogen sensing. The permeable membrane 94 separates the oil chamber 148 from the hydrogen sensing chamber 104. As the oil enters the chamber 152 through entry channel 156 the oil flows over the spiral grooves 158 of the stationary vortex generator 142. The oil therefore is directed toward the permeable number 94 and the turbulence removes bubbles or any debris that may have settled on the permeable member, thereby cleaning the permeable member 94 for good hydrogen transmission. It also assures continuous movement of oil through the chamber without stagnant areas of low circulation. The vortex generator 142 has grooves such as those in a drill bit. A preferred groove arrangement has been found to be that of a high flow machining drill. Flow of the oil from the chamber 54 takes place through oil exit passage 162, controlled by solenoid valves (not shown).

FIG. 25 is a schematic of the method and apparatus of the invention particularly for the sensor the embodiment of FIGS. 16-24. As shown, the oil flow is from the transformer oil supply, up through the oil pump down to an oil filter, and into the oil reservoir. In the oil reservoir moisture and temperature of the oil are sensed. Further oil sampling may take place. The oil solenoid valve controls oil flow out of the chamber and into the vortex generator of the hydrogen sensor. Oil flow solenoid 2 controls oil flow out of the hydrogen sensor for return to the transformer. The air pump supplies air through solenoid 3 into the hydrogen gas sensing area and out through air solenoid 4 for purging of the palladium in hydrogen sensor. The air passing through the head of the hydrogen sensor exits through air solenoid 4 to the atmosphere. The air and oil solenoids are closed during the about four hours required for hydrogen measurement.

There are variations of this invention which would be obvious to those of skill in the art. For instance, rather than making use of air in the refreshing of the palladium, oxygen could be used. Further, it would be well known to provide air filters for the air entering the hydrogen sensor. Other types of sensors also could be added to the test container, however the unit is intended to be small, low-cost, and compact so added features are not necessary. The invention unit typically is small, measuring less than 100 in.$^3$, not including the controller unit.

The invention claimed is:

1. A method of sensing hydrogen in a liquid comprising: providing a measuring device comprising a hydrogen sensing chamber and a palladium hydrogen sensor mounted in contact with said chamber, positioning a hydrogen permeable membrane between the liquid and the hydrogen sensor and creating a headspace, selectively providing air to the sensor headspace, thereby bringing air into contact with said palladium sensor to refresh the palladium, shutting off air flow to the sensor headspace, after the palladium sensor is refreshed bringing liquid into said chamber, allowing hydrogen to pass through the membrane and reach equilibrium, and reading the hydrogen concentration.

2. The method of claim 1 further comprising, bringing a known quantity of hydrogen into the headspace between the membrane and the palladium sensor for calibration of the hydrogen sensor prior to the hydrogen measurement.

3. The method of claim 1 wherein solenoid valves are utilized to allow air into the headspace and to remove air and hydrogen test gases from the headspace.

4. The method of claim 1 wherein the liquid comprises transformer oil.

5. The method of claim 1 wherein providing a membrane comprises providing a membrane made from tetrafluoroethylene.

6. The method of claim 1 wherein said measuring device further provides a moisture sensor on the measuring device to measure moisture content of the liquid.

7. The method of claim 1 comprising circulating the liquid to be tested through the hydrogen sensing chamber and moisture sensing compartment from a larger container and then returning the liquid to the larger container.

8. The method of claim 1 comprising providing the moisture sensing compartment with a moisture sensor extending into the liquid.

9. The method of claim 1 wherein said liquid comprises an oil.

10. The method of claim 1 wherein the bringing of liquid into the chamber utilizes of vortex generator to create turbulence on the membrane.

11. The method of claim 1 wherein liquid flow is stopped by solenoid valves during hydrogen measurement.

12. Apparatus for measuring hydrogen gas in a liquid comprising a measuring device, a palladium hydrogen sensor mounted on said device, a membrane separating said hydrogen sensor from liquid in hydrogen sensing chamber creating headspace, means to circulate gas to said hydrogen sensor to refresh the palladium, and means to shut off gas circulation to the hydrogen sensor.

13. The apparatus for measuring hydrogen gas of claim 12 further comprising means to bring hydrogen containing gas into the headspace between said membrane and said hydrogen sensor in order to calibrate said sensor.

14. Apparatus for measuring hydrogen gas of claim 12 wherein the measuring device further comprises a moisture sensor mounted in a moisture sensing compartment.

15. The apparatus for measuring hydrogen gas of claim 14 further comprising a controller for the hydrogen sensor.

16. The apparatus for measuring hydrogen gas of claim 13 further compromising a diaphragm pump to bring air to said head space, a check or solenoid valve for controlling air entry into said headspace, a check or solenoid valve for controlling air exit from said headspace.

17. The apparatus of claim 12 wherein said measuring device is provided with means to circulate liquid from a larger container into contact with the hydrogen sensor and return liquid to the larger container.

18. The apparatus of claim 17 wherein the means to circulate liquid from a larger container into contact with the sensor comprises a vortex generator to create turbulence on the membrane.

19. The apparatus of claim 12 wherein said measuring device further comprises a moisture sensing compartment.

20. The apparatus of claim 19 wherein the moisture sensing compartment is provided with a moisture sensor and a temperature sensor.

21. A sensor comprising a palladium hydrogen sensor, a membrane in contact with liquid, the membrane is separated from said sensor in order to create headspace, means for gas circulation in the headspace, and means to move the liquid into contact with the membrane and then seal a known quantity of liquid into contact with the hydrogen sensor.

22. The sensor of claim 21 further comprising a pump for gas circulation and a pump to move liquid through said sensor chamber.

23. The sensor of claim 21 further comprising solenoid valves to shut off air flow to said sensor.

24. The sensor of claim 21 wherein said membrane comprises a gas permeable tetrafluoroethylene.

25. The sensor of claim 21 further comprising a microcontroller for the palladium sensor.

26. The apparatus of claim 25 wherein said measuring device further comprises at least one heater.

27. The apparatus of claim 21 wherein means to move liquid into contact with said membrane comprises a vortex generator.

28. The apparatus of claim 21 wherein means to seal liquid into contact with the hydrogen sensor comprise solenoid valves.

* * * * *